(12) United States Patent
Kang et al.

(10) Patent No.: US 12,403,160 B2
(45) Date of Patent: Sep. 2, 2025

(54) INJECTION COMPOSITION CONTAINING ISOLATED MITOCHONDRIA, AND USE THEREOF

(71) Applicant: Paean Biotechnology Inc., Daejeon (KR)

(72) Inventors: Young-Cheol Kang, Wonju-si (KR); Kyuboem Han, Daejeon (KR); Sang-Min Lim, Incheon (KR); Hahnsun Jung, Gunpo-si (KR); Hye Jeong Hwang, Cheongju-si (KR); Junyoung Son, Seoul (KR)

(73) Assignee: Paean Biotechnology Inc., Daejeon (KR)

( * ) Notice: Subject to any disclaimer, the term of this patent is extended or adjusted under 35 U.S.C. 154(b) by 401 days.

(21) Appl. No.: 18/044,559

(22) PCT Filed: Aug. 10, 2021

(86) PCT No.: PCT/KR2021/010592
§ 371 (c)(1),
(2) Date: Mar. 8, 2023

(87) PCT Pub. No.: WO2022/055134
PCT Pub. Date: Mar. 17, 2022

(65) Prior Publication Data
US 2023/0270780 A1      Aug. 31, 2023

(30) Foreign Application Priority Data

Sep. 10, 2020   (KR) ........................ 10-2020-0116285

(51) Int. Cl.
| | |
|---|---|
| *A61K 35/12* | (2015.01) |
| *A61K 9/00* | (2006.01) |
| *A61K 9/08* | (2006.01) |
| *A61K 47/18* | (2017.01) |
| *A61K 47/26* | (2006.01) |

(52) U.S. Cl.
CPC ............ *A61K 35/12* (2013.01); *A61K 9/0019* (2013.01); *A61K 9/08* (2013.01); *A61K 47/183* (2013.01); *A61K 47/26* (2013.01)

(58) Field of Classification Search
CPC .................................................. A61K 9/0019
See application file for complete search history.

(56) References Cited

FOREIGN PATENT DOCUMENTS

| | | | |
|---|---|---|---|
| CN | 102046178 A | | 5/2011 |
| CN | 105012963 A | * | 11/2015 |
| KR | 10-2007-0085864 A | | 8/2007 |
| KR | 101504969 B1 | | 3/2015 |
| KR | 10-2018-0071030 A | | 6/2018 |
| KR | 10-2019-0061181 A | | 6/2019 |
| KR | 20190092348 A | | 8/2019 |
| KR | 102019277 B1 | | 9/2019 |
| KR | 10-2019-0124656 A | | 11/2019 |
| KR | 102111321 B1 | | 5/2020 |
| WO | WO 0050043 A1 | | 8/2000 |
| WO | WO 2007112757 A2 | | 10/2007 |
| WO | WO 2012102645 A2 | | 8/2012 |
| WO | WO 2018101708 A1 | | 6/2018 |
| WO | WO 2019209051 A1 | | 10/2019 |
| WO | 2020013108 A1 | | 1/2020 |

OTHER PUBLICATIONS

Kesner et al., "Characteristics of Mitochondrial Transformation into Human Cells," Sci. Rep. 6, 26057; doi: 10.1038/srep26057, May 17, 2016, 15 pages.

* cited by examiner

*Primary Examiner* — Qiuwen Mi
(74) *Attorney, Agent, or Firm* — Seed IP Law Group LLP

(57) ABSTRACT

Provided is a composition for injection containing isolated mitochondria. More specifically, provided is a liquid composition for injection containing glycine, saccharide, buffer, and mitochondria, and a pharmaceutical composition comprising the liquid composition for injection as an active ingredient. The liquid composition for injection according to the present disclosure is capable of securing the safety of a mitochondrial therapeutic and maintaining the activity of mitochondria, by enhancing the stability of mitochondria for prevention or treatment of mitochondria-related diseases and preventing and inhibiting formation of blood clots in the blood of a subject who is administered with the same. Accordingly, the pharmaceutical composition according to the present disclosure may solve the aggregation that may occur when mitochondria are administered in the body and thus enables to safely and effectively inject mitochondria into the body to be used for the purpose of preventing and treating various diseases caused by mitochondrial dysfunction.

16 Claims, 4 Drawing Sheets

INJECTION COMPOSITION CONTAINING ISOLATED MITOCHONDRIA, AND USE THEREOF

BACKGROUND

The present disclosure relates to a composition for injection containing isolated mitochondria and a use thereof. More particularly, the present disclosure relates to a liquid composition for injection containing glycine or glycine oligomer, saccharide, buffer, and mitochondria and a pharmaceutical composition containing the liquid composition for injection as an active ingredient.

As an energy source, mitochondria play a key role in various physiological processes such as ATP synthesis, production of reactive oxygen species, and apoptosis. Therefore, damage to mitochondria may result in various diseases, and most mitochondrial disorders are caused by inherited or acquired mutations that occur in mitochondrial DNA. For example, the functions of mitochondria may be modified by swelling due to abnormality in mitochondrial membrane potential, oxidative stress caused by reactive oxygen species, free radicals, etc., and defects in the function of oxidative phosphorylation for energy generation in mitochondria. As examples of such mitochondrial dysfunction, mitochondrial genetic disease, inflammatory disease (e.g., rheumatoid arthritis), ischemic disease, infectious disease, heart disease, myopathy, degenerative diseases (e.g., Parkinson's disease and Alzheimer's disease), occurrence of various cancers and metastasis thereof, etc. have been reported.

For the treatment of diseases associated with such mitochondrial dysfunction, attempts to isolate mitochondria from cells or tissues and inject them back into the living body for the purpose of treatment are increasing recently.

According to the increase of studies on mitochondria for their therapeutic use, to this end, studies on how to maintain the ex vivo stability of isolated mitochondria and efficient delivery of isolated mitochondria to target cells or tissues are also increasing.

However, the mitochondrial delivery therapy for mitochondria-related diseases has not yet been developed because there is a limitation on the range of treatment or there are problems of side effects when the isolated mitochondria are injected in vivo.

Effective delivery of mitochondria to a target cell or tissue is an important factor in the effectiveness of a mitochondria-containing drug for the treatment of mitochondria-related diseases. It has been reported that successful delivery of isolated mitochondria depends on the quantity and quality of mitochondria to be injected and the appropriate delivery route, and mitochondria may be efficiently delivered and absorbed into a target cell or tissue when they are not physically or functionally damaged.

Meanwhile, mitochondria may be delivered by a method of local injection, in which mitochondria are directly injected into a target organ, and a method of systemic administration, in which mitochondria are injected through vascular injection. The main safety concerns for the administration of mitochondria through vascular injection are formation of blood clots and blockage of microvessels. Even when vascular administration of cells such as a stem cell therapeutic, since the combination of the administered stem cells and platelets creates a blood clot thereby obstructing blood flow and reducing the oxygen supply to the cells, heparin as an anticoagulant is co-administered so as to reduce and resolve these problems. However, there was a report that heparin inhibits the intracellular delivery of mitochondria (E. E. Kesner et. al.), and thus, it is difficult to administer heparin concurrently during the vascular injection of mitochondria, and no suitable anticoagulant has yet been known.

As such, for the efficient delivery of a drug containing isolated mitochondria to a target cell or tissue, there is a need for the development of a special formulation for isolated mitochondria which may maintain ex vivo safety of a mitochondrial drug and solve platelet aggregation or blood clot formation, which are the side effects that occur when a drug is administered via intravascular injection.

DISCLOSURE

Technical Problem

Under the circumstances, the present inventors have made an extensive effort to develop an efficient formulation for injection for the delivery of a drug containing mitochondria, which is isolated for the treatment of mitochondria-related diseases, to cells or tissues. As a result, it was confirmed that the formulation for injection of the present disclosure may inhibit platelet aggregation or blood clot formation even without using an anticoagulant. Additionally, it was confirmed that the formulation for injection of the present disclosure not only inhibits the occurrence of mitochondrial aggregation, but also does not damage the activity of mitochondria, and it was confirmed that mitochondria may be stably administered into the body by injection, thereby completing the present disclosure.

Technical Solution

For the achievement of those purposes described above, in accordance with an embodiment, the present disclosure provides a liquid composition for injection containing glycine, saccharide, buffer, and mitochondria.

In accordance with another embodiment, the present disclosure also provides a pharmaceutical composition for preventing or treating mitochondria-related diseases containing the liquid composition for injection as an active ingredient.

In accordance with still another embodiment, the present disclosure also provides a method for preventing or treating mitochondria-related diseases, the method including administering the liquid composition for injection to a subject.

Advantageous Effects

The liquid composition for injection containing mitochondria according to the present disclosure, for preventing or treating mitochondrial dysfunction-related diseases, not only maintains the membrane potential and stability of mitochondria by inhibiting an aggregation when using mitochondria after isolating them from cells or tissues, but also makes it possible to secure the safety of mitochondria injection by inhibiting the formation of blood clots in the subject receiving the same. Since the composition according to the present disclosure may prevent the reduction of platelets and aggregation that may occur when isolated allogenic or autologous mitochondria are administered into the body, it is expected to significantly improve the commercial availability of mitochondrial injections by making it possible to broadly apply isolated mitochondria to the treatment of various diseases caused by deterioration in mitochondrial functions or mitochondrial dysfunction.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
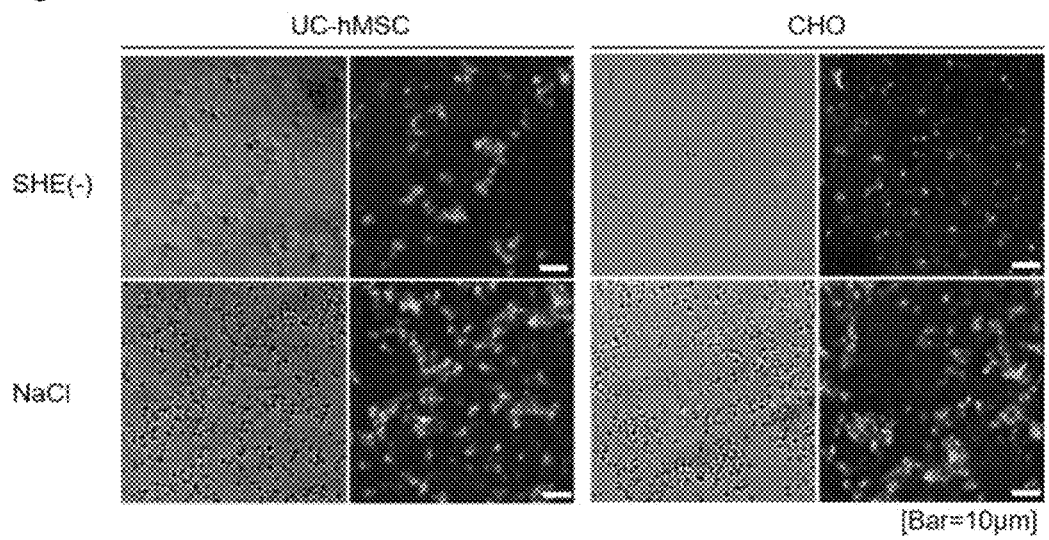
FIG. 1 shows images, in which the self-coagulated phenomenon of isolated mitochondria was observed, and the degree of aggregation of mitochondria isolated from human umbilical cord-derived mesenchymal stem cells (UC-hMSC) and Chinese hamster ovary-derived cells (CHO) was confirmed in a SHE storage solution (sucrose 250 mM, HEPES 20 mM (pH 7.4), and EGTA 2 mM) according to the present disclosure (in particular, a physiological NaCl solution (saline) used as an injection was used as a control)

Hereinafter, specific embodiments will be described in detail with reference to the accompanying drawings.
Liquid Composition for Injection Containing Mitochondria In an aspect, the present disclosure provides a liquid composition for injection which contains glycine or oligomer thereof, saccharide, buffer, and mitochondria.

As used herein, the term "mitochondria" refers to an organelle of a eukaryotic cell involved in the synthesis and regulation of adenosine triphosphate (ATP), which is an intracellular energy source, and it is associated with the control of various metabolic pathways in vivo (e.g., cell signaling, cell differentiation, apoptosis, cell cycle, and cell growth). Therefore, it has been reported that deterioration of mitochondrial function or mitochondrial dysfunction due to genetic, environmental, or unknown causes is associated with the occurrence of various diseases, such as mitochondria-related genetic diseases, inflammatory diseases (e.g., rheumatoid arthritis), ischemic diseases, infectious diseases, heart diseases, muscular diseases, degenerative diseases (e.g., Parkinson's disease and Alzheimer's disease), various kinds of cancer, cancer metastasis, etc.

The liquid composition for injection of the present disclosure is a composition for the prevention or treatment of diseases related to mitochondrial functions, and when mitochondria are administered by injection, it may inhibit the formation of blood clots that may be caused by mitochondrial aggregation, reduction and aggregation of platelets, etc., may maintain and/or enhance the stability of mitochondria, and may also stably maintain the activity of mitochondria.

The liquid composition for injection of the present disclosure may contain glycine or oligomer thereof, saccharides, buffer, and mitochondria.

The glycine oligomer refers to an oligomer to which one or more glycine is binding. The glycine oligomer may be 2 to 20 glycine. Specifically, the glycine oligomer may contain 1, 2, 3, 4, 5, 6, 7, 8, 9, 10, 11, 12, 13, 14, 15, 16, 17, 18, 19, or 20 glycine. Additionally, the glycine oligomer may contain 2 to 10 or 3 to 5 glycine. In an example, the glycine oligomer may be glycine dimer or glycine trimer.

The glycine or oligomer thereof may be present at a concentration of 1 mM or more in the lipid composition for injection. Additionally, the glycine or oligomer thereof may be preferably present at a concentration of 15 mM or more in the lipid composition for injection. Specifically, the glycine or oligomer thereof may be present at a concentration of 15 mM to 150 mM, a concentration of 17 mM to 130 mM, a concentration of 20 mM to 120 mM, a concentration of 22 mM to 110 mM, or a concentration of 25 mM to 100 mM. Specifically, the glycine or oligomer thereof may be present at a concentration of about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, or about 90 mM.

Additionally, the glycine, although not limited thereto, may be used together with one or more amino acids selected from the group consisting of histidine, isoleucine, leucine, lysine acetate, methionine, phenylalanine, threonine, tryptophan, valine, alanine, arginine, aspartic acid, cysteine, glutamic acid, proline, serine, and tyrosine.

Additionally, the glycine may be used together with glycine monomer and glycine oligomer. In an embodiment, the glycine monomer and glycine dimer may be used together in the lipid composition for injection. Additionally, the glycine monomer and glycine trimer may be used together in the lipid composition for injection. Additionally, the glycine dimer and glycine trimer may be used together in the lipid composition for injection. Additionally, the glycine monomer, glycine dimer, and glycine trimer may be used together in the lipid composition for injection.

The saccharide contained in the liquid composition for injection of the present disclosure, although not limited thereto, may be one or more selected from the group consisting of sucrose, trehalose, mannitol, sorbitol, glucose, fructose, mannose, maltose, lactose, isomaltose, dextran, and dextrin. In particular, the saccharide may be trehalose, mannitol, or sucrose. Preferably, the saccharide may be trehalose.

The buffer contained in the liquid composition for injection of the present disclosure, although not limited thereto, may be selected from the group consisting of Tris buffer, hydroxyethyl piperazine ethane sulfonic acid (HEPES) buffer, 3-(N-morpholino)propanesulfonic acid (MOPS) buffer, and a buffer containing acetate or phosphate. Preferably, the buffer may be an injectable Tris buffer.

The pH of the buffer, although not limited thereto, may be in the range of about 6.3 to about 9.5. Additionally, the pH may be in the range of about 7.0 to about 7.8, or about 7.2 to about 7.6. Preferably, the pH may be in the range of about 7.3 to about 7.5.

Additionally, the buffer, although not limited thereto, may be present in the liquid composition for injection at a concentration of 5 mM to 50 mM, a concentration of 8 mM to 40 mM, a concentration of 10 mM to 35 mM, a concentration of 13 mM to 30 mM, or a concentration of 15 mM to 25 mM.

The liquid composition for injection of the present disclosure may be administered parenterally. In this case, the parenteral administration may be performed by methods such as vascular administration, subcutaneous administration, mucosal administration, muscle administration, articular administration, ocular administration, etc. In an embodiment of the present disclosure, the composition may preferably be administered by vascular injection.

Additionally, the liquid composition for injection of the present disclosure may have an osmolarity in the range of 200 mOsm to 400 mOsm, 230 mOsm to 380 mOsm, 250 mOsm to 350 mOsm, 260 mOsm to 320 mOsm, 270 mOsm to 330 mOsm, or 280 mOsm to 300 mOsm.

The osmolarity in the ranges described above facilitates long-term storage at temperatures of 2° C. to 8° C. or higher, while enabling the composition to be suitable for administration without causing side effects in a subject through parenteral administration (e.g., intravascular, intramuscular, or subcutaneous injection).

As used herein, the term "osmolarity" refers to the number of moles of a solute contributing to the osmotic pressure of a solution per kilogram of a solvent, and osmolarity is determined by measuring the freezing point depression of a sample using an osmometer.

The subject, although not limited thereto, may be a mammal, such as a human, dog, cow, horse, pig, sheep, goat, cat, mouse, rabbit, and rat, and preferably a human.

Additionally, the liquid composition for injection may further contain a chelating agent. The chelating agent, although not limited thereto, may be one or more selected from the group consisting of an injectable grade of ethylene glycol tetraacetic acid (EGTA), ethylene diamine tetraacetic acid (EDTA), and 1,2-bis(o-aminophenoxy)ethane-N,N,—N',N', tetra-acetic acid (BAPTA).

The chelating agent may remove damage caused by ion leakage after obtaining mitochondria contained in the liquid composition for injection.

In the liquid composition for injection of the present disclosure, the mitochondria may be those obtained from eukaryotes and may be those obtained from mammals or humans. Specifically, the mitochondria may be those isolated from cells or tissues. For example, the mitochondria may be those obtained from somatic cells, germ cells, or stem cells, and may be those isolated from blood cells or platelets. Additionally, the mitochondria may be used after concentrating tissues or cells followed by disruption and isolation, or the mitochondria may be those isolated from a tissue or cell sample, which was thawed after cryopreservation, after thawing and disruption.

Specifically, the somatic cells may be muscle cells, hepatocytes, neurons, fibroblasts, epithelial cells, adipocytes, osteocytes, leukocytes, lymphocytes, platelets, or mucosal cells.

Additionally, the stem cells are undifferentiated cells having the potential to differentiate into various types of tissue cells, and although not limited thereto, may be any one selected from the group consisting of mesenchymal stem cells, adult stem cells, induced pluripotent stem cells, embryonic stem cells, bone marrow stem cells, neural stem cells, limbal stem cells, and tissue-derived stem cells. In particular, the mesenchymal stem cells may be those obtained from any one selected from the group consisting of umbilical cord, umbilical cord blood, bone marrow, fat, muscle, nerve, skin, synovial fluid, testis, amniotic membrane, and placenta.

In addition, the mitochondria may be those isolated from cells or tissues cultured ex vivo, or those isolated from a sample which was thawed after cryopreservation.

Additionally, the mitochondria may be those obtained from an autologous, allogenic, or xenogenic species. Specifically, autologous mitochondria refer to mitochondria obtained from tissues or cells of the same subject. Additionally, allogenic mitochondria refer to mitochondria which are obtained from a subject belonging to the same species while having different genotypes for alleles. Additionally, xenogenic mitochondria refer to mitochondria which are obtained from a subject belonging to a different species.

Meanwhile, in the case of isolating the mitochondria from a specific cell, for example, mitochondria may be isolated by various modified methods of those including various known methods such as using a specific buffer solution or a potential difference and a magnetic field.

The mitochondria isolation may be obtained by disrupting cells and centrifuging from the aspect of maintaining mitochondrial activity. In a specific embodiment, the isolation may be performed in the following steps: culturing cells and performing a first centrifugation of the composition containing the cells to produce a pellet; resuspending the pellet in a buffer solution and homogenizing the resultant; performing a second centrifugation of the homogenized solution to prepare a supernatant; and performing a third centrifugation of the supernatant to purify the mitochondria. In particular, it is preferable from the aspect of maintaining cell activity that the time during which the second centrifugation is performed is adjusted to be shorter than the time for which the first and third centrifugations are performed. The centrifugation speed may be increased from the first centrifugation to the third centrifugation.

Specifically, the first to third centrifugations may be performed at a temperature of 0° C. to 10° C., preferably at a temperature of 3° C. to 5° C. Additionally, the centrifugation may be performed for 1 to 50 minutes and the centrifugation time may be appropriately adjusted according to the number of centrifugations, the content of a sample, etc.

In addition, the first centrifugation may be performed at a speed of 100×g to 1,000×g, 200×g to 700×g, or 300×g to 450×g. Additionally, the second centrifugation may be performed at a speed of 1×g to 2,000×g, 25×g to 1,800×g, or 500×g to 1,600×g. Additionally, the third centrifugation may be performed at a speed of 100×g to 20,000×g, 500×g to 18,000×g, or 800×g to 15,000×g.

The liquid composition for injection of the present disclosure may be stored in a container selected from the group consisting of vials, cartridges, syringes, and autoinjectors.

Additionally, the container in which the liquid composition for injection of the present disclosure is stored may be stored at room temperature, at a refrigerated temperature of 2° C. to 8° C., or 25° C. to 40° C. until the composition is administered to a subject in need of treatment.

The subject, although not limited thereto, may be a mammal, such as a human, dog, cow, horse, pig, sheep, goat, cat, mouse, rabbit, or rat, and preferably a human.

The liquid composition for injection, although not limited thereto, may be parenterally administered, for example, by vascular administration, subcutaneous administration, mucosal administration, muscular administration, ocular administration, or intraperitoneal administration using an 18 G to 32 G needle with a volume of 5 mL or less, 3 mL or less, or 2 mL or less.

Use of Liquid Composition for Injection Containing Mitochondria

In another aspect, the present disclosure provides a pharmaceutical composition for preventing or treating diseases which contains liquid composition for injection containing isolated mitochondria. In particular, the use of the pharmaceutical composition may be to prevent or treat mitochondria-related diseases.

As used herein, the term "mitochondria-related diseases" collectively refers to diseases involving deterioration of mitochondrial functions or mitochondrial dysfunction due to genetic, environmental, or unknown causes. For example, these diseases include genetic diseases (e.g., Leber's hereditary optic neuropathy (LHON), Leigh syndrome, myoclonic epilepsy associated with ragged-red fibers (MERRF), mitochondrial myopathy, encephalopathy, hyperlactacidemia, and mitochondrial myopathy, encephalopathy, lactacidosis, stroke (MELAS), etc.); degenerative neurological diseases (e.g., Parkinson's disease and Alzheimer's disease); metabolic diseases (e.g., diabetes and obesity); and inflammatory diseases (e.g., sepsis, rheumatoid arthritis, etc.).

The pharmaceutical composition of the present disclosure containing isolated mitochondria as an active ingredient, although not limited thereto, may prevent or treat any one disease selected from the group consisting of sepsis (KR 10-2019-0050017 A), cancer (KR 10-2126199 B1), heart disease, rheumatoid arthritis (KR 10-2019-0094124 A), ischemic disease (KR 10-2019277 B1), infectious disease (KR 10-2018-0054523 A), Parkinson's disease, Alzheimer's disease, and muscle disease (KR 10-2019-0090754 A).

Specifically, the cancer, although not limited thereto, may be stomach cancer, liver cancer, lung cancer, colon cancer, breast cancer, prostate cancer, ovarian cancer, pancreatic cancer, uterine cervical cancer, thyroid cancer, laryngeal cancer, acute myeloid leukemia, brain tumor, neuroblastoma, retinoblastoma, head and neck cancer, salivary gland cancer, lymphoma, etc.

Additionally, the ischemic disease, although not limited thereto, may be severe limb ischemia, ischemic stroke, ischemic heart disease, ischemic colitis, etc. In particular, the ischemic disease may be a disease caused by mitochondrial abnormality, and it includes all of the ischemic cell disorders caused by deterioration in mitochondrial functions.

Additionally, the infectious disease, although not limited thereto, may be hepatitis B, hepatitis C, human papilloma virus (HPV) infection, cytomegalovirus infection, viral respiratory disease, influenza virus infection, etc.

Additionally, the muscle disease, although not limited thereto, may be MELAS syndrome, MERRF syndrome, Kearns-Sayre syndrome, myopathy, encephalomyopathy, myasthenia, myasthenia gravis, amyotrophic lateral sclerosis, muscular dystrophy, muscular atrophy, hypotonia, muscle weakness, muscle stiffness, etc. In particular, the muscle disease may include any muscle cell disorders caused by decreased mitochondrial function.

As used herein, the term "prevention" refers to any action that inhibits the occurrence of mitochondria-related diseases or delays the onset of mitochondria-related diseases through the administration of the pharmaceutical composition. As used herein, the term "treatment" refers to any action that improves or beneficially changes the symptoms of mitochondria-related diseases through the administration of the pharmaceutical composition.

The pharmaceutical composition may comprise a therapeutically effective amount or a pharmaceutically effective amount.

As used herein, the term "therapeutically effective amount" or "pharmaceutically effective amount" refers to an amount of a composition effective for preventing or treating a target disease, and also refers to an amount which is sufficient to treat a disease with a reasonable benefit/risk ratio applicable to a medical treatment, and does not cause side effects. The level of the effective amount may be determined according to factors including health conditions of a patient, kinds of disease, severity, a drug activity, sensitivity to drugs, an administration method, an administration time, an administration route, an excretion rate, a treatment duration, a combination, or concurrently used drugs, and other factors well known in the medical field.

In the pharmaceutical composition of the present disclosure containing a liquid composition for injection, the mitochondria, although not limited thereto, may be contained at a concentration of 0.1 µg/mL to 500 µg/mL, 0.2 µg/mL to 450 µg/mL, or 0.5 µg/mL to 400 µg/mL. By containing the mitochondria in the above range, it becomes easy to adjust the mitochondrial dose when the pharmaceutical composition is administered, the degree of symptom improvement in patients' mitochondria-related diseases (e.g., cancer, inflammatory diseases, neurodegenerative diseases, metabolic diseases, infectious diseases, muscular diseases, heart diseases, ischemic diseases, etc.) may be further improved. In particular, the dose of mitochondria may be quantified by quantifying the membrane protein of the isolated mitochondria from the blood, cells, tissues, etc. Specifically, the isolated mitochondria may be quantified by the Bradford protein assay (James D. McCully, J. Vis. Exp. 2014; (91): 51682).

In particular, as the pharmaceutical composition according to the present disclosure, mitochondria may be administered in an amount of 0.01 mg/kg to 5 mg/kg, 0.1 mg/kg to 4 mg/kg, or 0.25 mg/kg to 2.5 mg/kg based on the body weight of the subject for one administration, but is not limited thereto. That is, it is most preferred from the aspect of cell activity that, as the pharmaceutical composition, mitochondria be administered in an amount within the above range based on the body weight of the subject in which the mitochondria-related disease is caused.

Additionally, the pharmaceutical composition may be administered 1 to 10 times, 3 to 8 times, or 5 to 6 times, and preferably 5 times. In particular, the administration interval may be 1 to 7 days or 2 to 5 days, and preferably at intervals of 3 days.

As used herein, the term "administration" refers to the process of a certain material into a subject by any suitable method, and the administration route of the composition may be administered via any general route as long as the composition may reach the target tissue. Preferably, it may parenteral administration, but although not limited thereto, e.g., intraperitoneal administration, intravascular administration, muscular administration, mucosal administration, subcutaneous administration, intradermal administration, ocular administration, etc.

Additionally, the pharmaceutical composition according to the present disclosure may be administered to humans or other mammals, in which mitochondria-related diseases may be caused or which are suffering from such disease or disorder.

Accordingly, the pharmaceutical composition according to the present disclosure may be prepared as an injection that is physically and chemically very stable by adjusting the pH using a buffer that may be used for injection so as to secure product stability according to the distribution of injection prescriptions.

Specifically, the pharmaceutical composition of the present disclosure may contain water for injection. The water for injection is distilled water which is prepared to dissolve a solid injection or to dilute a water-soluble injection, and it may be a glucose injection, xylitol injection, D-mannitol injection, fructose injection, physiological saline, dextran 40 injection, dextran 70 injection, amino acid injection, Ringer's solution, lactic acid-Ringer's solution or Tris with a pH ranging from 3.5 to 8, HEPES, citric acid, phosphate buffer, sodium dihydrogen phosphate-citrate buffer, etc.

Additionally, the pharmaceutical composition of the present disclosure may contain a stabilizing agent or solubilizing agent. For example, the stabilizing agent may be pyrosulfite or ethylene diaminetetraacetic acid, and the solubilizing agent may be hydrochloric acid, acetic acid, potassium phosphate hydroxide, potassium hydrogen carbonate, potassium carbonate, or Tris.

In a specific embodiment, the pharmaceutical composition may contain a mixed preservation solution (e.g., a trehalose-Tris-glycine (TTG) solution) and may be commonly used in pharmaceutically acceptable pharmaceutical preparations. As an additive of the pharmaceutical composition, antioxidants, ATP, magnesium, etc., which are effective for maintaining and active mitochondrial function, may be contained.

In a further aspect, the present disclosure provides a use of the pharmaceutical composition for the prevention or treatment of the mitochondria-related diseases. Then, the pharmaceutical composition may be the liquid composition for injection. In this regard, the liquid composition for injection, the mitochondria-related disease, prevention, and treatment are aforementioned.

In a further aspect, the present disclosure provides a method for preventing or treating diseases, which includes administering the pharmaceutical composition described above to a subject.

Then, the liquid composition for injection, administration, administration dose, prevention, and treatment are aforementioned. The subject may be a patient suffering from a disease or an individual likely to have the disease. The subject may be a mammal, and preferably a human.

Additionally, the liquid composition for injection may be an injection that may be administered vascularly or may be an injection that may be administered locally.

The disease is a mitochondria-related disease, and specific diseases are as described above. In particular, the administration may be one which is performed via intra-venous, intra-muscular, or intra-dermal administration. Through this, the pharmaceutical composition according to the present disclosure may supply isolated mitochondria with normal activity directly to the lesion where the disease has occurred, thus being useful for increasing the activity of cells with deterioration in mitochondrial functions or for regenerating cells with mitochondrial dysfunction, and may be used for the prevention or treatment of the mitochondria-related diseases described above.

In a still further aspect, the present disclosure provides a use of the liquid composition for injection for the manufacture of a medicament for the prevention or treatment of the mitochondria-related disease. In this regard, the pharmaceutical composition, the mitochondria-related disease, prevention, and treatment are aforementioned.

MODE FOR INVENTION

Hereinafter, the present disclosure will be described in more detail through the following Example. However, these Examples are for illustrative purposes of the present disclosure, and the scope of the present disclosure should not be limited to these Examples.

Preparation Example 1. Cell Culture

Each of human umbilical cord-derived mesenchymal stem cells (UC-hMSCs) and human bone marrow-derived mesenchymal stem cells (BM-hMSCs) were each inoculated into an alpha-minimum essential medium (α-MEM, Gibco) medium, which contains 10% fetal bovine serum (FBS, Gibco), 100 µg/mL of streptomycin, and 100 U/mL of penicillin, and cultured for 72 hours.

A Chinese hamster ovary-derived cell line (i.e., CHO cells) were inoculated in the Dulbecco's modified eagle's medium (DMEM, Gibco) medium containing 10% fetal bovine serum (FBS, Gibco) and cultured for 72 hours.

L6 cells (American Type Culture Collection, ATCC, CRL-1458), which are a myoblast cell line derived from rat skeletal muscle, were inoculated into Dulbecco's modified eagle's medium-high glucose (DMEM-high glucose) containing 10% fetal bovine serum (FBS, Gibco), and cultured for 72 hours.

After the respective culture of cells were completed, respective cells were washed twice using Dulbecco's phosphate buffered saline (DPBS, Gibco). Thereafter, cells were obtained by treatment with 0.25% Trypsin-EDTA (TE). The obtained cells were resuspended to a cell concentration of $1\times10^7$ cells/mL so as to extract mitochondria.

Preparation Example 2. Obtaining Platelets

Preparation Example 2.1. Isolation of Platelets from Whole Blood of Pigs

Pig whole blood was centrifuged at 300×g for 5 minutes to obtain a cloudy yellow supernatant containing platelets and plasma. The obtained supernatant was centrifuged at 1,500×g for 15 minutes to obtain a platelet precipitate (pellet). The obtained platelet precipitate was replaced with an equal amount of Dulbecco's phosphate-buffered saline (DPBS) solution, washed by centrifugation at 1,500×g for 15 minutes, and resuspended in an equal amount of a fresh DPBS solution.

Preparation Example 2.2. Isolation of Platelets from Human Whole Blood

A yellow supernatant was obtained by centrifuging human whole blood containing K2-dipotassium ethylenediaminetetraacetic acid (EDTA) at 300×g for 3 minutes. The obtained supernatant was centrifuged at 1,500×g for 15 minutes to obtain a platelet precipitate (pellet). The obtained platelet precipitate was resuspended in Dulbecco's phosphate-buffered saline (DPBS) solution.

Example 1. Isolation and Storage of Mitochondria

Example 1.1. Isolation of Mitochondria

Respective cultures including the cells cultured in Preparation Example 1 were centrifuged at 380×g for 3 minutes to remove the supernatant. The recovered cells were mixed with a DPBS solution and centrifuged at 1,100×g for 3 minutes. In particular, the subsequent processes were all performed under refrigeration temperature conditions, including the solution used.

After removing the supernatant and adding a homogenization buffer, the cells were resuspended, transferred to a fresh tube, and the cells were disrupted and homogenized by a physical method using a 1 mL syringe. The resulting supernatant was recovered by centrifuging the homogenate obtained by disrupting the cells at 2,000×g at a temperature of about 4° C. for 10 minutes. The recovered supernatant was centrifuged again at 2,000×g. The supernatant obtained after centrifugation was centrifuged at 12,000×g for 10 minutes to recover a mitochondrial precipitate.

The solution of Table 1 was added to the recovered mitochondria precipitate as a storage buffer for mitochondria, centrifuged at 12,000×g for 10 minutes, and the supernatant was removed. The supernatant was removed such that the precipitated mitochondria were not lost, and the storage buffer for mitochondria was re-added, and the mixture was centrifuged again at 12,000×g to completely remove the supernatant. After the supernatant was completely removed, the composition for mitochondria storage of Table 1 below was added to the obtained precipitated mitochondria and resuspended.

TABLE 1

| | | Composition (mM) | | | | | |
|---|---|---|---|---|---|---|---|
| | | 1 | 2 | 3 | 4 | 5 | 6 |
| Buffer | Tris | 20 | 20 | 20 | 20 | 20 | — |
| | HEPES | — | — | — | — | — | 20 |
| Saccharide | D-Mannitol | 195 | — | — | — | — | — |
| | D-Trehalose | — | 195 | — | 195 | 195 | — |
| | Sucrose | — | — | 195 | — | — | 250 |
| Amino Acid | Glycine | 65 | 65 | 65 | — | — | — |
| Chelating | K-EDTA | — | — | — | — | 2 | — |
| Agent | EGTA | — | — | — | — | — | 2 |

Example 1.2. Isolation Using a Stabilizing Formulation of Mitochondria

When mitochondria were separated from cells, SHE solution (sucrose 250 mM, HEPES 20 mM (pH 7.4), and EGTA 2 mM) was used. Specifically, to the cells of animals and humans cultured or being cultured in Preparation Example 1 above, buffer solutions #1 to #6 of the composition as in Table 1, which consist of a saccharide (sucrose, mannitol, or trehalose), a buffer (HEPES or Tris), chelating agents (EGTA or EDTA), and an amino acid, were added and resuspended. Then, after disrupting the cells in the same manner as in Example 1.1., mitochondria were obtained from the cells.

Example 2. Observation of Self-Aggregation of Isolated Mitochondria

Example 2.1. Staining and Storage of Mitochondria

The concentration of mitochondria was measured by taking a part of the isolated mitochondria solution and using the bicinchoninic acid (BCA) assay to measure a protein concentration. 50 μg of the isolated mitochondria were stained with 100 nM at 4° C. for 10 minutes using MitoTracker Green (Molecular Prove, Eugene, OR), which is a mitochondria-specific green marker. 50 μg of the mitochondria were treated per 1 mL of each solution and the resultants were each stored at 4° C. in a solution state in a confocal dish. After 16 hours, the degree of self-aggregation of mitochondria was observed in a confocal dish state using a confocal laser scanning microscope (CarlZeiss, Germany). In particular, the isolated mitochondria were tested by storing them in physiological saline or SHE solution.

Example 2.2. Confirmation of Aggregation of Isolated Mitochondria

In order to confirm the phenomenon of self-aggregation of mitochondria induced in a storage solution of mitochondria isolated from cells, after isolation of mitochondria derived from human umbilical cord-derived mesenchymal stem cells (UC-hMSC) and Chinese hamster ovary-derived cells (CHO), the isolated mitochondria were each stored in the SHE storage solution (sucrose 250 mM, HEPES 20 mM (pH 7.4), and EGTA 2 mM) and NaCl solution (saline). After 16 hours of storage, the aggregation of the isolated mitochondria itself was confirmed with a confocal laser scanning microscope.

As a result, as shown in FIG. 1, mitochondrial aggregation was formed in saline NaCl solution (saline) which is used as an injection solution. Therefore, in the case of mitochondria, since the phenomenon of mitochondrial aggregation occurs when using saline containing a high concentration of sodium salt as an injection solution, it was found that a stable storage buffer that does not cause aggregation should be used.

Example 3. Observation of Platelet Aggregation Induced by Mitochondria

In order to observe the platelet aggregation induced by mitochondria isolated from cells, mitochondria were isolated from human umbilical cord-derived mesenchymal stem cells (UC-hMSC), human bone marrow-derived mesenchymal stem cells (BM-hMSC), rat skeletal muscle-derived cell line (L6), and platelet cells, and stained with MitoTracker DeepRed, which is a mitochondria-specific dark red marker.

In particular, the platelets resuspended in a DPBS solution in Preparation Example 2 were stained with 0.5 μM of MitoTracker Green, which is a mitochondria-specific green marker, at room temperature for 10 minutes, and then washed with a DPBS solution.

Figure 2A:
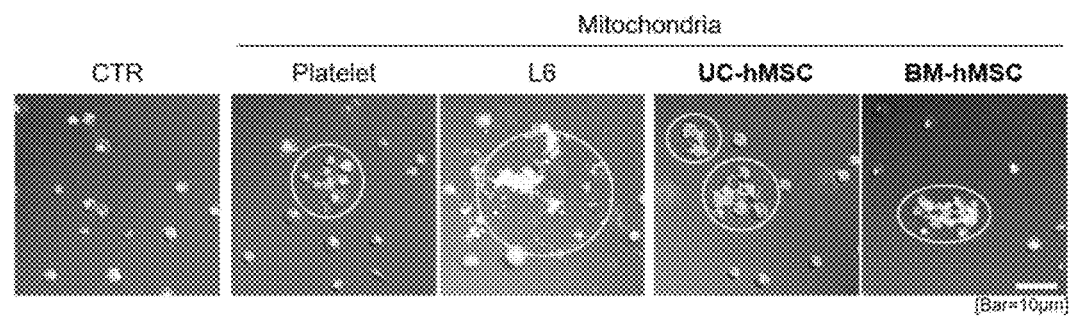
FIG. 2a shows images, in which platelet aggregation caused by mitochondria isolated from various cells was observed ex vivo, and it was confirmed that platelet aggregation was induced by mitochondria obtained from platelets isolated from human umbilical cord-derived mesenchymal stem cells (UC-hMSC), human bone marrow-derived mesenchymal stem cells (BM-hMSC), rat skeletal muscle-derived cell line (L6), or the whole blood (in particular, CTR refers to a control not treated with mitochondria)

After treating 5 μg of the stained mitochondria with 1 mL of a platelet solution ($10^7$/mL), the resultant was incubated with shaking at 37° C. at 100 rpm for one hour. After dispensing 3 μL of the mitochondria-treated platelets on a slide glass, it was covered with a cover glass and observed using a confocal laser scanning microscope (CarlZeiss, Germany) (FIG. 2a).

As a result, all of the mitochondria isolated from the platelets, rat skeletal muscle-derived cell line (L6), human umbilical cord-derived mesenchymal stem cells (UC-hMSC), and human bone marrow-derived mesenchymal stem cells (BM-hMSC) could induce platelet aggregation. From this, it was found that when mitochondria are injected into blood vessels, it has an inherent risk to induce platelet aggregation, thereby causing a decrease in the number of platelets or the formation of blood clots. In particular, the isolated mitochondria were used in the experiment by storing in physiological saline.

Example 4. Confirmation of Effects of Storage Solvent for Mitochondria and Antithrombotic Agent on Inhibition of Platelet Aggregation In order to confirm the effect of a storage solvent for mitochondria and an antithrombotic agent on inhibition of platelet aggregation, the mitochondria of human umbilical cord-derived mesenchymal stem cells (UC-hMSC) were isolated and stored in saline and SHE solution, which is a storage solvent, for one hour, respectively, and the resultant was treated with the platelets isolated from pig whole blood and then treated with heparin. After 1 hour, the result was confirmed with a confocal laser scanning microscope.

Figure 2B:
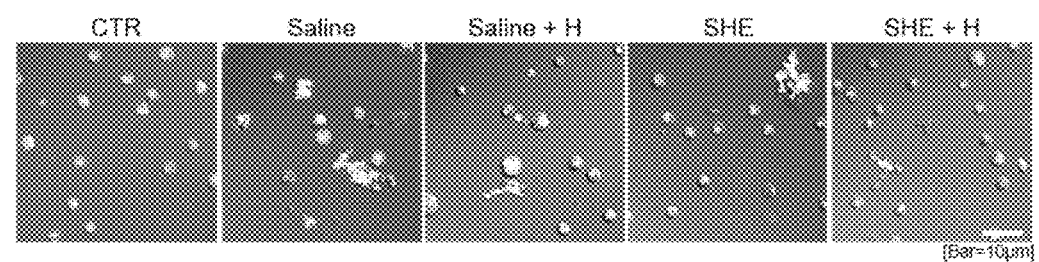
FIG. 2b shows images, in which it was confirmed that mitochondria isolated from human umbilical cord-derived mesenchymal stem cells (UC-hMSC), which were stored in saline or SHE storage solution, induced platelet aggregation. In particular, it was confirmed that platelet aggregation was partially inhibited during the treatment with heparin (H) as an antithrombotic agent.
Figure 3:
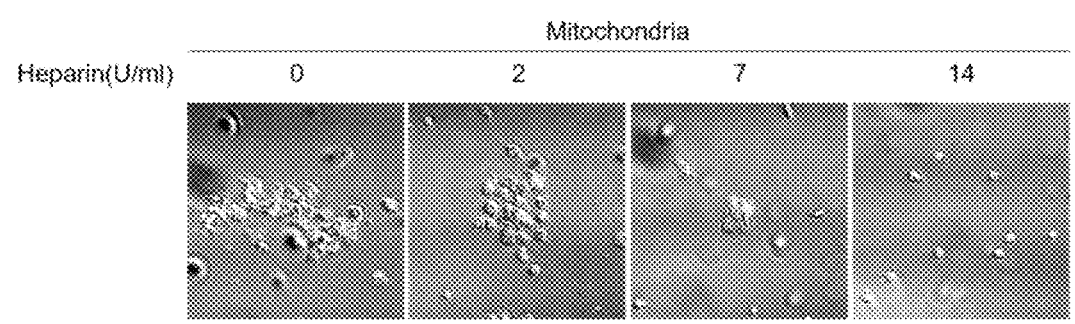
FIG. 3 shows images, in which the inhibitory effect of platelet aggregation by an antithrombotic agent was confirmed, and it was confirmed that when platelets isolated from whole blood were simultaneously treated with heparin and mitochondria, platelet aggregation induced by mitochondria was inhibited according to the increase in heparin concentration.

As shown in FIG. 2b, the mitochondria, which were derived from human umbilical cord-derived mesenchymal stem cells (UC-hMSC) and stored in saline and SHE solution, increased platelet aggregation and the aggregation was partially inhibited when treated with heparin. Additionally, as shown in FIG. 3, it was found that when the platelets were treated with the mitochondria, which were derived from human umbilical cord-derived mesenchymal stem cells (UC-hMSC) ans were stored in SHE solution, platelet aggregation induced by mitochondria was inhibited as the concentrations of heparin as an antithrombotic agent increased.

Example 5. Buffer Screening for Formulation for Mitochondria Injection

Changes in the number of platelets in the blood according to the composition of the injection solution and the presence/absence of an anticoagulant, when the mitochondria isolated from human umbilical cord-derived mesenchymal stem cells (UC-hMSC) were administered once to BALB/c-nu/nu mice by intravenous injection (50 μg/0.3 mL), were compared and evaluated. The specific experimental design, which was performed so as to confirm the effect of reducing the number of platelets during intravascular injection of mitochondria into mice, is as shown in Table 2 below.

TABLE 2

| Experimental Group | Buffer To Be Administered | Remarks |
|---|---|---|
| PBS | Saline | Excipient Control |
| UC-PBS | Saline | UC mitochondria-PBS |
| UC-PBS + Heparin | Saline | UC mitochondria-PBS + Heparin (10 IU/head) |
| UC-TTB | Tris-Trehalose | UC mitochondria-TTB |
| UC-TTB + Heparin | Tris-Trehalose | UC mitochondria-TTB + Heparin |
| UC-SHE | HEPES-Sucrose-EDTA | UC mitochondria-SHE |

Figure 4:
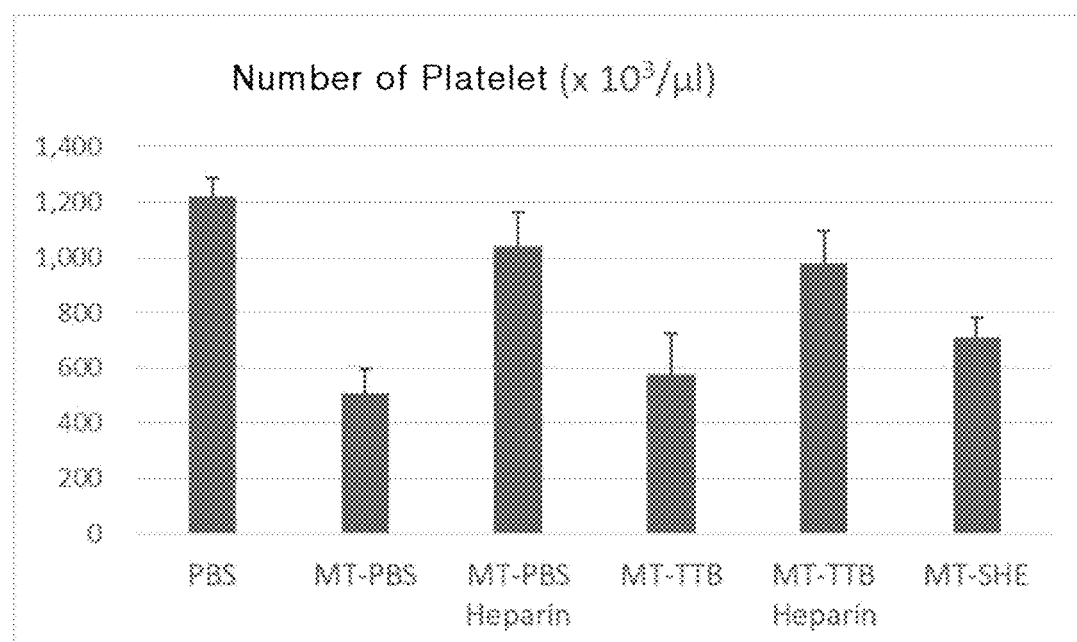
FIG. 4 shows a graph, in which the change in the number of platelets according to the formulation for vascular injection of mitochondria was confirmed, and in which the changes in the number of platelets in the blood according to the composition of an injection solution and the presence or absence of an anticoagulant were compared when an intravenous injection of mitochondria isolated from human umbilical cord-derived mesenchymal stem cells (UC-hMSC) was administered into a mouse model (in particular, MT represents mitochondria, TTB represents a Tris-trehalose buffer solution, and SHE represents a Sucrose-HEPES-EGTA buffer solution)

It was confirmed that when saline was used in the composition of the injection, the number of platelets decreased was highest, whereas the number of platelets was decreased less in the injection solution containing sucrose or trehalose. Additionally, when heparin was added, the decrease in platelets was recovered to some extent, but the decrease in platelets was not completely inhibited (FIG. 4).

Example 6. Effects of Glycine Concentration on Mitochondria Activity

In the composition for stabilizing mitochondria described in Example 1, an attempt was made to determine the effect of glycine concentration on mitochondrial activity.

Figure 5:
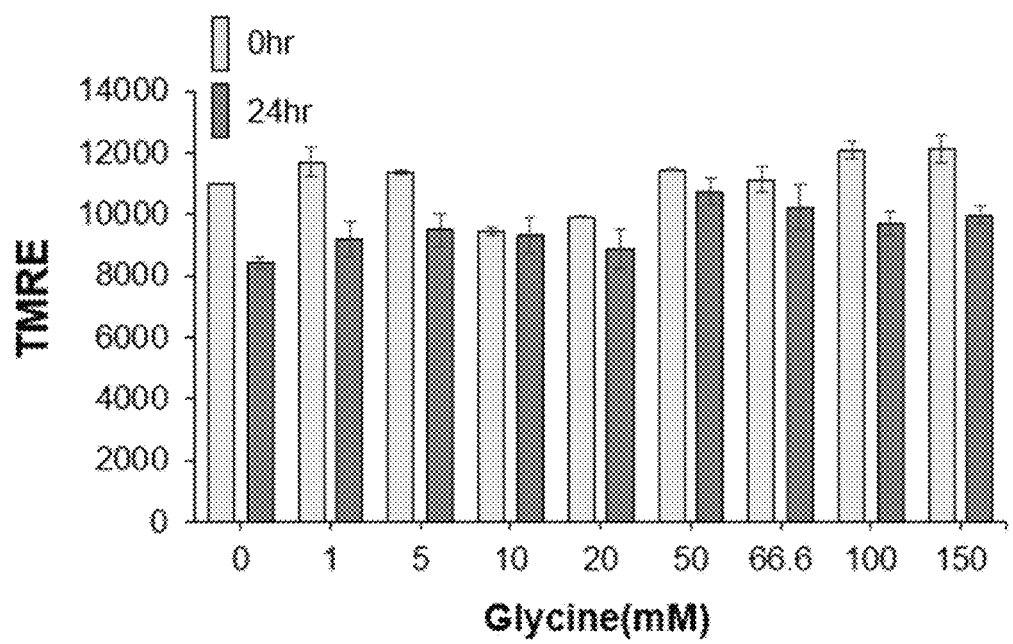
FIG. 5 shows a graph, in which the effect of the composition according to the present disclosure on the level of mitochondrial activity according to the concentration of glycine in the composition was confirmed, and in which the changes in fluorescence value of a membrane potential marker for mitochondria were measured after mitochondria were stored for 24 hours in solutions containing glycine at various concentrations were measured (in particular, TMRE refers to tetramethylrhodamine ethyl ester as a membrane potential marker for mitochondria)

First, mitochondria were isolated by the isolation method described in Example 1 above, and the isolated mitochondria were stained with tetramethylrhodamine ethyl ester (TMRE) as a mitochondrial membrane potential marker, and then washed. After washing, the resulting mitochondria were stored in each solution, where the concentration conditions of solution 2 of Example 1 and Tris (20 mM) and trehalose (195 mM) were set in the same manner, whereas the concentration of glycine was adjusted variously in the range of 0 mM to 150 mM. After storing for 24 hours, the changes in fluorescence value were measured (FIG. 5).

Example 7. Effects of Glycine on Inhibition of Platelet Aggregation

Figure 6:
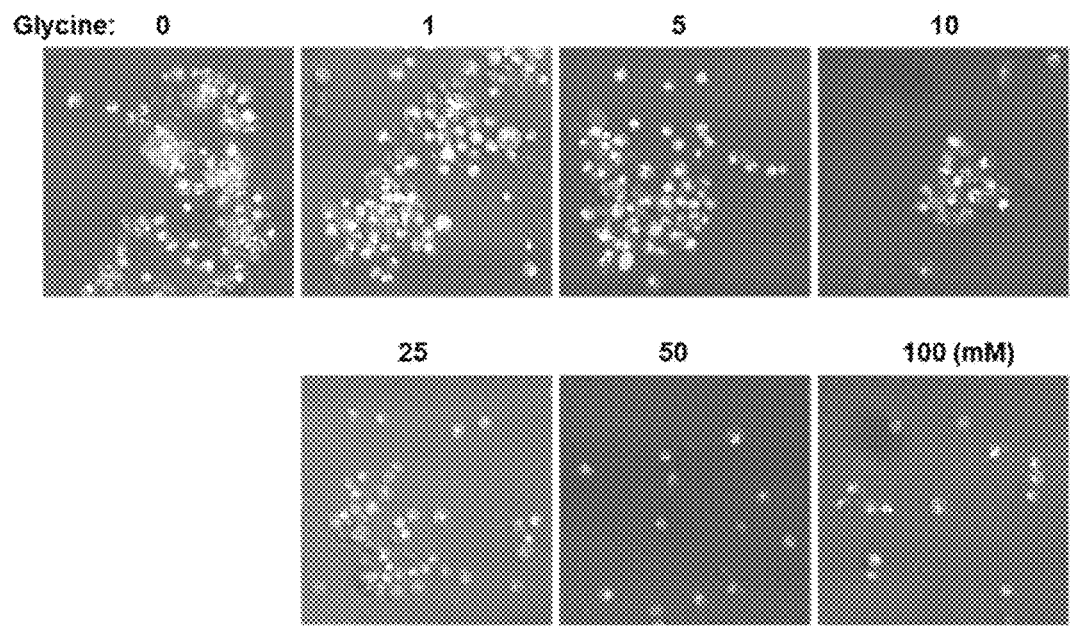
FIG. 6 shows images, in which the effect of inhibiting platelet aggregation by mitochondria due to glycine contained in the composition according to the present disclosure was confirmed, and in which it was confirmed that platelet aggregation induced by mitochondria can be inhibited when glycine is present at a concentration of 25 mM or higher in the composition of the present disclosure.

In order to confirm the inhibitory effect of mitochondria on platelet aggregation according to glycine as an amino acid, mitochondria were first isolated from human umbilical cord-derived mesenchymal stem cells (UC-hMSC), and then stained with MitoTracker DeepRed, which is a mitochondria-specific dark red marker. Thereafter, 1 μg of the stained mitochondria were suspended in the composition solution with 10 μL of Tris-trehalose buffer (TTB) glycine at each concentration (0 mM, 1 mM, 5 mM, 10 mM, 25 mM, 50 mM, and 100 mM), refrigerated for one hour, and treated with 1 mL of a platelet solution ($10^7$/mL). After treatment, the resultant was incubated with shaking at 100 rpm at 37° C. for one hour. 3 μL of mitochondria-treated platelets were observed using a confocal laser scanning microscope (CarlZeiss, Germany) (FIG. 6).

As a result, it was found that mitochondria could not inhibit platelet aggregation at a low concentration of glycine, but the aggregation was gradually inhibited in the experimental groups in which glycine was present at a concentration of 25 mM or higher. From the above results, it could be inferred that glycine can effectively inhibit platelet aggregation induced by mitochondria.

Figure 7:
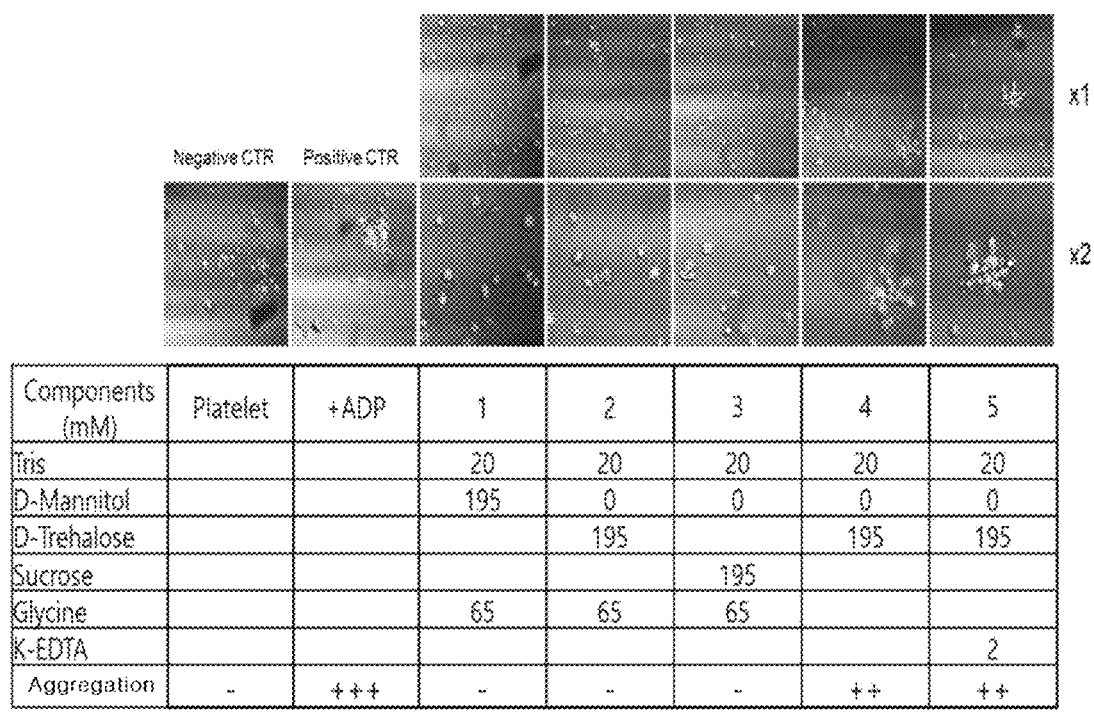
FIG. 7 shows images and a table, in which the inhibitory effect of the mitochondrial composition formulation containing glycine according to the present disclosure on platelet aggregation, and in which it was confirmed that mitochondria do not cause platelet aggregation in the glycine-containing composition of the present disclosure compared to the composition in which glycine is not added.

Example 8. Effects of Mitochondrial Composition Formulation Containing Glycine on Platelet Aggregation In order to confirm the inhibitory effect of a mitochondrial composition formulation containing glycine as an amino acid against platelet aggregation, mitochondria were first isolated from human umbilical cord-derived mesenchymal stem cells (UC-hMSC) and then stained with MitoTracker DeepRed, which is a mitochondria-specific dark red marker. Then, 1 μg of the stained mitochondria were suspended in 10 μL of Tris buffer (specific compositions of 1, 2, 3, 4, and 5 are shown in FIG. 7) and treated with 1 mL of a platelet solution ($10^7$/ml). After treatment, the resultant was incubated with shaking at 100 rpm at 37° C. for one hour. 3 μL of the mitochondria-treated platelets were observed using a confocal laser scanning microscope (CarlZeiss, Germany) (FIG. 7).

As a result, it was confirmed that even if there is a difference in the type of saccharides (sucrose, trehalose, and mannitol) among the major components for mitochondrial stabilization without the platelet aggregation, platelet aggregation was not observed in the compositions in which glycine was added with respect to all three types of sugars. However, in the compositions in which glycine was not added, platelet aggregation was induced by mitochondria.

Example 9. Effects of Glycine on Human Platelet Aggregation

In order to observe the platelet aggregation induced by mitochondria isolated from cells, after mitochondria were isolated from human umbilical cord-derived mesenchymal stem cells (UC-hMSC), they were stained with MitoTracker DeepRed, which is a mitochondria-specific dark red marker. In particular, the platelets resuspended in a DPBS solution in Preparation Example 2 were stained at room temperature for 10 minutes using 0.5 μM MitoTracker Green, which is a mitochondrial-specific green marker, and washed with a DPBS solution.

1 μg of the stained mitochondria were suspended in 10 μL of Tris-trehalose-glycine (TTG) buffer, Tris-trehalose-glycine-glycine (TTG-G) buffer, or Tris-trehalose-glycine-glycine-glycine (TTG-G-G) buffer, kept refrigerated for one hour, and then treated with 1 mL of a platelet solution ($10^7$/mL).

Figure 8:
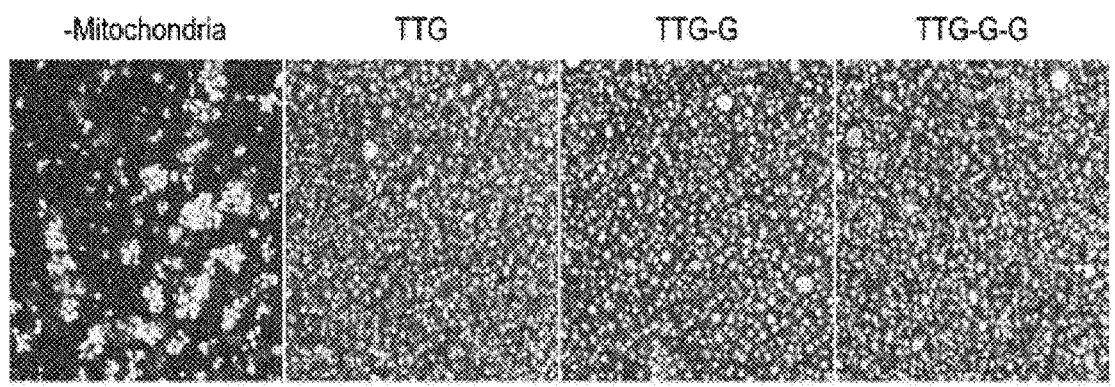
FIG. 8 shows a table, in which the inhibitory effect of the mitochondrial composition formulation containing glycine or oligomer thereof according to the present disclosure on platelet aggregation, and in which it was confirmed that mitochondria do not cause platelet aggregation in the glycine oligomer-containing composition of the present disclosure compared to the composition in which glycine is not added.

After treatment, the resultant was incubated with shaking at 100 rpm at 37° C. for one hour. 3 μL of the mitochondria-treated platelets were dispensed on a slide glass, covered with a cover glass, and observed using a confocal laser scanning microscope (CarlZeiss, Germany) (FIG. 8).

As a results, it is confirmed that no platelet aggregation was observed in glycine dimer and glycine trimer as well as glycine monomer. Therefore, it was confirmed that the glycine oligomer is a major component for mitochondrial stabilization without platelet aggregation.

Although the composition for injection containing isolated mitochondria and use thereof have been described with reference to the specific embodiments, they are not limited thereto. Therefore, it will be readily understood by those skilled in the art that various modifications and changes can be made thereto without departing from the spirit and scope of the present disclosure defined by the appended claims.

What is claimed is:

1. A liquid composition for injection comprising an effective amount of glycine, saccharide, buffer, and mitochondria.

2. The liquid composition of claim 1, wherein the glycine is glycine monomer or glycine oligomer.

3. The liquid composition of claim 2, wherein the glycine oligomer is glycine dimer or glycine trimer.

4. The liquid composition of claim 1, wherein the glycine has a concentration of 15 mM to 150 mM.

5. The liquid composition of claim 1, wherein the saccharide is one or more selected from the group consisting of sucrose, trehalose, mannitol, sorbitol, glucose, fructose, mannose, maltose, lactose, isomaltose, dextran, and dextrin.

6. The liquid composition of claim 5, wherein the saccharide is trehalose, mannitol, or sucrose.

7. The liquid composition of claim 1, wherein the buffer is selected from the group consisting of Tris buffer, hydroxyethyl piperazine ethane sulfonic acid (HEPES) buffer, 3-(N-morpholino) propanesulfonic acid (MOPS) buffer, and a buffer comprising acetate or phosphate.

8. The liquid composition of claim 6, wherein the buffer is Tris buffer.

9. The liquid composition of claim 1, wherein the buffer has a pH of 7.0 to 7.8.

10. The liquid composition of claim 1, wherein the buffer has a concentration of 5 mM to 50 mM.

11. The liquid composition of claim 1, wherein the composition has an osmolarity of 200 mOsm to 400 mOsm.

12. The liquid composition of claim 1, wherein the mitochondria are isolated from a eukaryotic cell or tissue.

13. The liquid composition of claim 12, wherein the cell is any one selected from the group consisting of somatic cell, a germ cell, a stem cell, a blood cell, a platelet, and combinations thereof of a mammalian or human.

14. A pharmaceutical composition for treating or reducing the incidence of mitochondrial dysfunction diseases comprising the liquid composition for injection according to claim 1.

15. The pharmaceutical composition of claim 14, wherein the disease is mitochondrial dysfunctional disease selected from the group consisting of chronic inflammatory disease, acute inflammatory disease, ischemic disease, neurological disease, heart disease, muscular disease, degenerative disease, metabolic disease, fibrotic disease, joint disease, eye disease, hair loss, and immune-related disease.

16. A method for treating or reducing the incidence of a mitochondrial dysfunction disease in a subject in need thereof, said method comprising: administering the liquid composition for injection according to claim 1 to the subject.

* * * * *